(12) United States Patent
Elliott et al.

(10) Patent No.: US 11,642,177 B2
(45) Date of Patent: May 9, 2023

(54) SPINAL IMPLANT SYSTEM AND METHOD

(71) Applicant: WARSAW ORTHOPEDIC INC., Warsaw, IN (US)

(72) Inventors: John A. Elliott, Atoka, TN (US); Julien J. Prevost, Memphis, TN (US); Daniel Paxton Wall, Cordova, TN (US); Mark R. Grizzard, Munford, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 276 days.

(21) Appl. No.: 17/010,086

(22) Filed: Sep. 2, 2020

(65) Prior Publication Data

US 2020/0397513 A1  Dec. 24, 2020

Related U.S. Application Data

(63) Continuation of application No. 16/163,688, filed on Oct. 18, 2018, now Pat. No. 10,799,300.

(51) Int. Cl.
| | | |
|---|---|---|
| *A61B 17/70* | (2006.01) | |
| *A61B 34/20* | (2016.01) | |
| *A61B 34/30* | (2016.01) | |
| *A61B 90/00* | (2016.01) | |
| *A61B 17/00* | (2006.01) | |

(52) U.S. Cl.
CPC .......... *A61B 34/20* (2016.02); *A61B 17/7074* (2013.01); *A61B 34/30* (2016.02); *A61B 90/361* (2016.02); *A61B 17/00234* (2013.01); *A61B 2017/00477* (2013.01); *A61B 2034/2051* (2016.02); *A61B 2034/2055* (2016.02); *A61B 2034/303* (2016.02); *A61B 2034/305* (2016.02)

(58) Field of Classification Search
CPC ............ A61B 17/7074–7082; A61B 17/2034; A61B 17/2055; A61B 17/70
See application file for complete search history.

(56) References Cited

U.S. PATENT DOCUMENTS

| | | | |
|---|---|---|---|
| 6,021,343 A | 2/2000 | Foley et al. | |
| 6,190,395 B1 | 2/2001 | Williams | |
| 6,198,961 B1 | 3/2001 | Stern et al. | |
| 6,235,038 B1 | 5/2001 | Hunter et al. | |
| 6,402,762 B2 | 6/2002 | Hunter et al. | |
| 6,468,202 B1 | 10/2002 | Irion et al. | |
| 6,477,400 B1 | 11/2002 | Barrick | |

(Continued)

OTHER PUBLICATIONS

International Search Report and Written Opinion of the International Searching Authority, Korean Intellectual Property Office, PCT/US2019/055564, dated Jan. 28, 2020.

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

A surgical instrument comprises a first member including a drive engageable with a first mating surface of a bone fastener. A second member is rotatable relative to the first member and includes an element engageable with a second mating surface of the bone fastener. The members are engageable with the bone fastener in a release configuration, an intermediate configuration and a locked configuration. Systems, surgical adaptors, spinal implants and methods are disclosed.

21 Claims, 9 Drawing Sheets

(56) References Cited

U.S. PATENT DOCUMENTS

| | | |
|---|---|---|
| 6,478,802 B2 | 11/2002 | Kienzle, III et al. |
| 6,491,699 B1 | 12/2002 | Henderson et al. |
| 6,556,857 B1 | 4/2003 | Estes et al. |
| 6,565,577 B2 | 5/2003 | Cosman |
| 6,584,339 B2 | 6/2003 | Galloway, Jr. et al. |
| 6,585,651 B2 | 7/2003 | Nolte et al. |
| 6,605,095 B2 | 8/2003 | Grossman |
| 6,694,168 B2 | 2/2004 | Traxel et al. |
| 6,725,080 B2 | 4/2004 | Melkent et al. |
| 6,725,082 B2 | 4/2004 | Sati et al. |
| 6,752,812 B1 | 6/2004 | Truwit |
| 6,796,988 B2 | 9/2004 | Melkent |
| 7,072,707 B2 | 7/2006 | Galloway, Jr. et al. |
| 7,204,840 B2 | 4/2007 | Skakoon et al. |
| 9,918,752 B2 | 3/2018 | Hennard et al. |
| 10,799,300 B2 * | 10/2020 | Elliott .................... A61B 34/20 |
| 2011/0046683 A1 * | 2/2011 | Biedermann ...... A61B 17/7082 |
| | | 606/305 |
| 2013/0296950 A1 | 11/2013 | Landry et al. |
| 2014/0031872 A1 | 1/2014 | Jackson |
| 2014/0052180 A1 | 2/2014 | Justis et al. |
| 2015/0105833 A1 * | 4/2015 | Simpson ............ A61B 17/8875 |
| | | 606/86 R |
| 2015/0250521 A1 * | 9/2015 | Poker ................ A61B 17/8875 |
| | | 606/104 |
| 2016/0262809 A1 * | 9/2016 | May ................... A61B 17/7082 |
| 2017/0172589 A1 * | 6/2017 | Peters ................ A61B 17/1757 |
| 2018/0303522 A1 * | 10/2018 | Wall ....................... A61B 34/20 |

* cited by examiner

SPINAL IMPLANT SYSTEM AND METHOD

CROSS-REFERENCE TO RELATED APPLICATIONS

This application is a continuation of U.S. patent application Ser. No. 16/163,688, filed Oct. 18, 2018, which is incorporated herein by reference, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member including a drive engageable with a first mating surface of a bone fastener. A second member is rotatable relative to the first member and includes an element engageable with a second mating surface of the bone fastener. The members are engageable with the bone fastener in a release configuration, an intermediate configuration and a locked configuration. In some embodiments, systems, surgical adaptors, spinal implants and methods are disclosed.

In one embodiment, the surgical instrument comprises an outer tubular sleeve including a drive engageable with a socket of a bone fastener shaft. An inner shaft is rotatable relative to the sleeve and includes a screw connectable with an inner threaded surface of a bone fastener receiver. Indicia of an orientation of the members with the bone fastener includes an eject position, a partially threaded position and a fully threaded position. The indicia includes a window of the first member and a marker of the second member.

In one embodiment, the surgical instrument comprises a first member including a window and a drive engageable with a first mating surface of a bone fastener. A second member is rotatable relative to the first member and includes an element engageable with a second mating surface of the bone fastener. The second member further includes a marker. The marker is movable relative to the window to display an indicia of a release configuration, an intermediate configuration and a locked configuration of the members with the bone fastener.

BRIEF DESCRIPTION OF THE DRAWINGS

The present disclosure will become more readily apparent from the specific description accompanied by the following drawings, in which.

DETAILED DESCRIPTION

Figure 1:
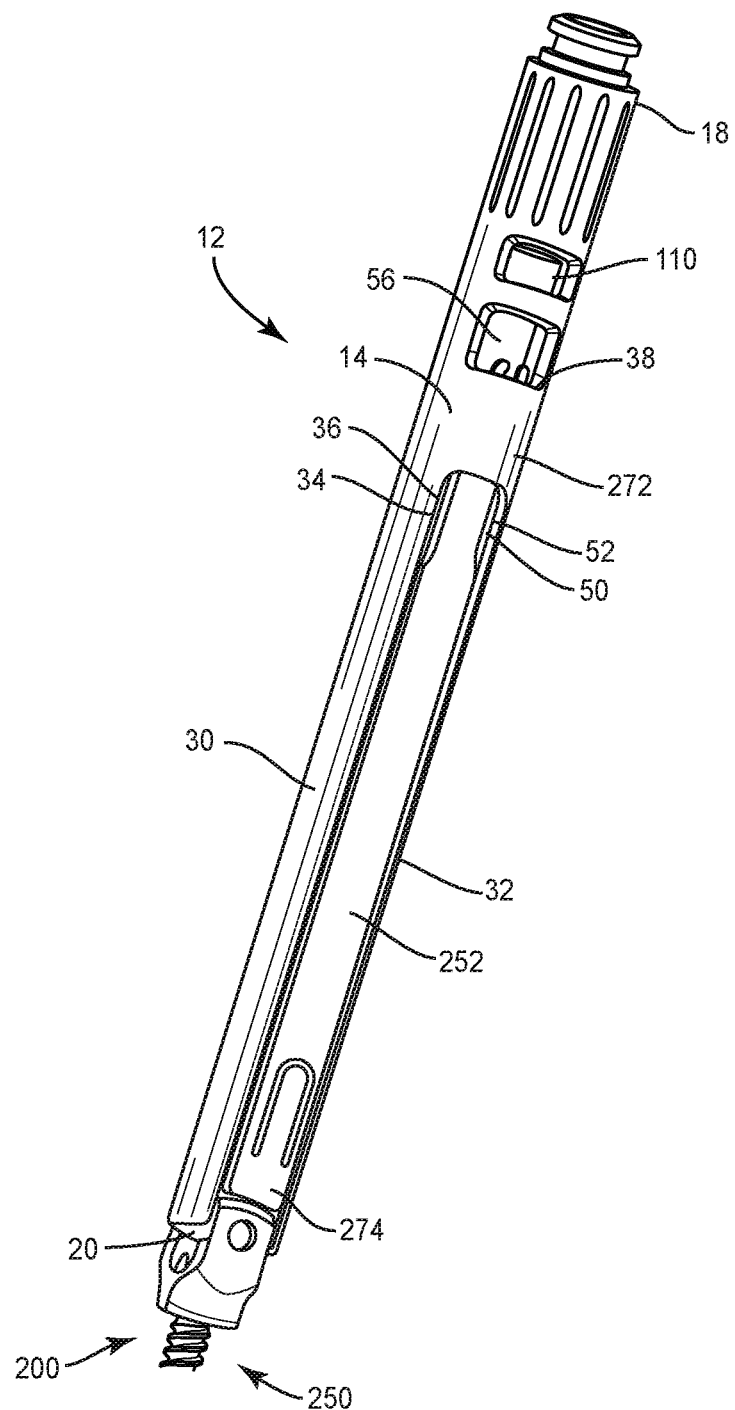
FIG. 1 is a perspective view of components of one embodiment of a surgical system in accordance with the principles of the present disclosure.
Figure 2:
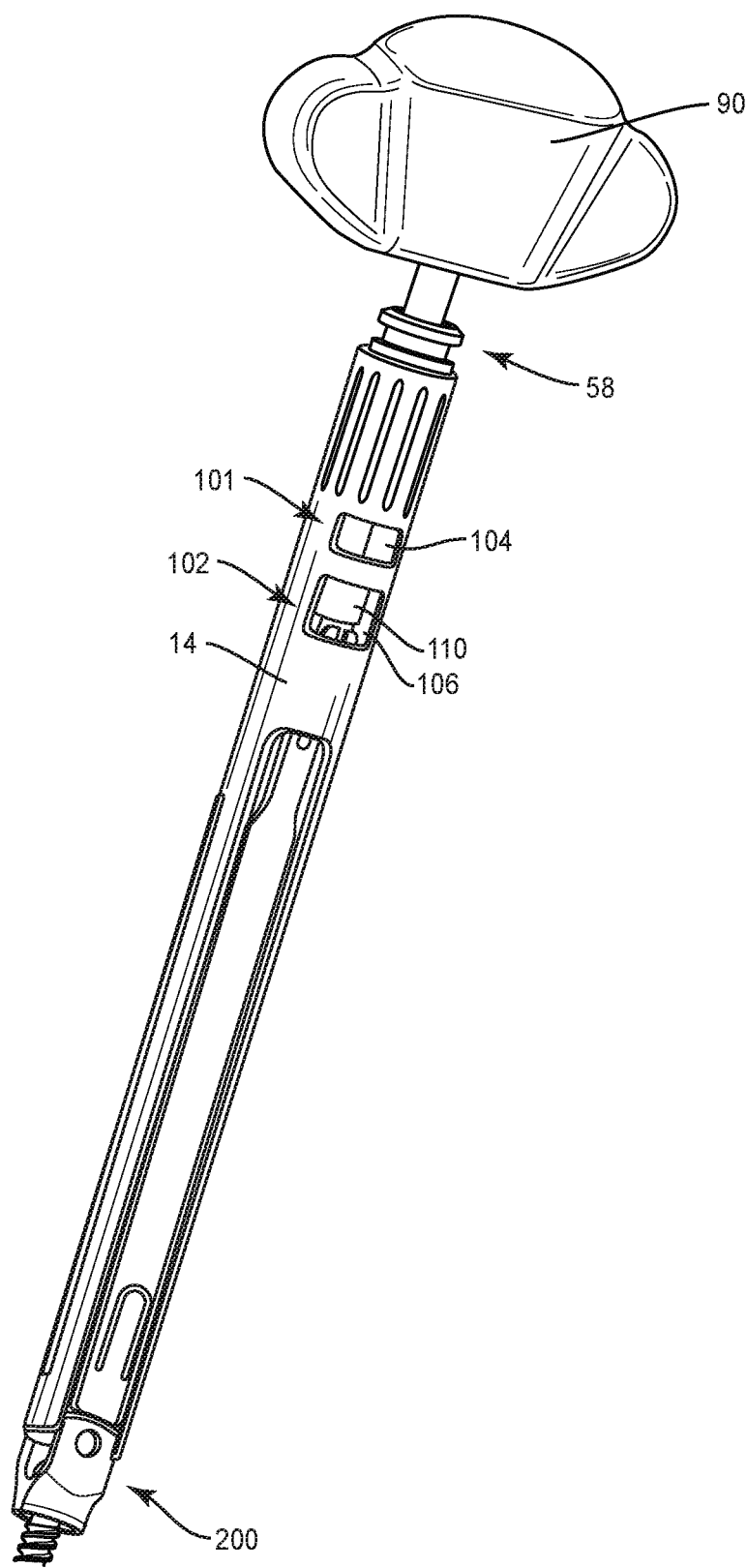
FIG. 2 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a sleeveless surgically navigated driver. In some embodiments, the present surgical system comprises a surgical instrument that comprises a sleeveless surgically navigated driver employed with a surgical robotic guidance system. In some embodiments, the driver can be connected with extended tabs of a bone screw. In some embodiments, the driver can be connected with a break-away adapter. In some embodiments, the driver can be connected with fenestrated screws connectable with bone filler device (BFD) attachments. In some embodiments, the driver can be employed with a bone screw that provides bi-cortical fixation to enhance fixation with vertebrae and reduce the risk of screw loosening when used with a biologic or agent, for example, bone cement (PMMA), and/or reduce the risk of biologic or agent leakage outside of a vertebral body.

In some embodiments, the present surgical system comprises a surgical instrument that comprises a screw driver. In some embodiments, the driver is configured for use with a spinal implant, such as, for example, a bone fastener or screw. The bone fastener may include open tulip head receivers and/or closed tulip head receivers. In some embodiments, the driver can be employed with a posted screw, a pedicle screw, a bolt, a bone screw for a lateral plate, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS) or a sacral bone screw.

In some embodiments, the present surgical system comprises a surgical driver instrument that comprises an internal thread to align/tighten a bone screw to the driver. In some embodiments, the driver employs a navigated break away adapter that provides a shortened over-all length of the driver and streamlines multiple-screw placement. In some embodiments, the driver includes a tip configured to mate with ATS, MAS, and SAS fenestrated screws. In some embodiments, the present surgical system comprises a surgical driver instrument employed with a handle. In some embodiments, the handle can be employed to tighten/align bone screws with the driver. In some embodiments, the handle can be used as a punch configured to displace material, for example, cement, which may become trapped in the driver tip.

In some embodiments, the present surgical system comprises a surgical driver instrument that includes an internal thread capture of a receiver of a bone screw. In some embodiments, the present surgical system comprises a surgical driver instrument that is engageable with driver tips for ATS, MAS and SAS bone screws. In some embodiments, the surgical driver instrument comprises a removable handle configured to tighten/align a screw to the driver. In some embodiments, the handle includes a tip configured as a punch that avoids cement overflow for fenestrated screws.

In some embodiments, the present surgical system comprises a surgical instrument that comprises a screw driver with a disengagement feature. In some embodiments, the driver is configured for use with a spinal implant, such as, for example, a bone fastener. The bone fastener may include open tulip head receivers and/or closed tulip head receivers. In some embodiments, the driver includes an inner thread to retain the bone fastener with the driver. In some embodiments, the screw driver is employed with robotic guidance. In some embodiments, the driver includes an inner shaft having a Torx tip configured for engagement with the bone fastener.

In some embodiments, the present surgical system comprises a surgical instrument that comprises a screw driver that can be employed with bone fasteners and one or more implant supports for treating a spine. In some embodiments, the present surgical system includes a surgical instrument that can easily connect and disconnect from a bone fastener. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver having an outer shaft and a drive tip that engages a bone fastener. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the present surgical system includes a screw driver having an internal retention mechanism. In some embodiments, the retention mechanism is fixed with a receiver of a bone fastener to resist and/or prevent disengagement of the retention mechanism from the receiver, for example, due to connection or friction with the end effector or tissue.

In some embodiments, the present surgical system includes a screw driver for use with robotic surgery. In some embodiments, the screw driver can be employed with FAS, UAS, SAS, TSAS and MAS, and allows the screws to be driven through a robotic end effector. In some embodiments, the screw driver includes a one piece outer sleeve having a tip. In some embodiments, the screw driver includes an internal retaining device that prevents accidental disengagement and/or unthreading.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a handle that is connected to a retention screw that threads into the bone screw. In some embodiments, the present surgical system includes tab extenders connected to the screw driver and prevented from extending outside the outside diameter of the screw driver by engaging undercuts of the screw driver. This configuration prevents an interference or hang-up if the bone screw needs to be removed through the end effector.

In some embodiments, the present surgical system comprises a surgical driver instrument that includes indicia, for example, a window and/or visual indicia configured to display translation of an inner shaft relative to an outer sleeve and the bone screw. In some embodiments, the indicia includes one or markers that can be aligned with one or more markers to indicate positioning of the inner shaft relative to the bone screw between a release configuration and a locked configuration of the surgical driver with the bone screw. In some embodiments, the driver includes visual confirmation of an intermediate configuration, for example, a flexible or loosened state of the driver with the bone screw. For example, during lumbar surgeries, a vertebral curve can cause engagement and/or interference between adjacent drivers due to driver rigidity between the driver and the bone screw.

In some embodiments, the surgical driver instrument includes indicia configured to display an intermediate configuration comprising the inner shaft being partially threaded with the bone fastener. In some embodiments, the indicia is configured to display the surgical driver being fully engaged in the locked configuration such that the inner shaft is fully engaged with the bone screw to form a rigid connection between the driver and the bone screw. In some embodiments, the indicia is configured to display a non-locking configuration such that the inner shaft is fully disengaged from the bone screw. In some embodiments, between a locking configuration and a non-locking configuration there is an area of partially engaged or a flexible or loosened state of the driver with the bone screw in which the driver is attached to the screw head threads, but not in a rigid state, for example, the bone fastener receiver is movable relative to the bone fastener screw shaft. In some embodiments, this configuration allows the driver to use the multi-axial range of motion of the bone screw to allow the driver to counter the engagement and/or interference between adjacent drivers. In some embodiments, the indicia displays the partially engaged and/or intermediate configuration such that the driver can be tightened to the locking configuration, or loosened to the non-locking configuration, for ejecting the driver from the bone screw.

In some embodiments, the outer sleeve includes indicia, such as, for example, a marking or scoring. In some embodiments, a marking or scoring of the outer sleeve is configured for alignment with a marking or scoring of an extender tab of a bone screw assembly. In some embodiments, alignment of the marking or scoring displays and/or indicates a selected alignment and connection of the surgical driver instrument with the bone screw assembly.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, for example, a driver 12. Driver 12 includes a member, such as, for example, a tubular outer sleeve 14 and a member, such as, for example, an inner shaft 56 configured for translation and/or rotation relative to outer sleeve 14. The components of driver 12 are configured for engagement and/or orientation with a bone fastener 200 for capture and release during a surgical procedure, which may include a release configuration, an intermediate configuration and a locked configuration, as described herein. Driver 12 includes indicia configured for displaying and/or indicating engagement and/or orientation of the components of driver 12, for example, inner shaft 56 and outer sleeve 14, with bone fastener 200. In some embodiments, driver 12 can be employed with an end effector of a robotic arm R (FIG. 9) to facilitate implant with robotic arm R. Driver 12 is guided through the end effector for guide-wireless insertion of a spinal implant, such as, for example, bone fastener 200, as described herein. See also, the examples and disclosure of surgical instruments, spinal implant systems and methods shown and described in commonly owned and assigned U.S. patent application Ser. No. 16/163,666 filed Oct. 18, 2018, and published as U.S. Patent Application Publication 20200121397, on Apr. 23, 2020, the entire contents of which being incorporated herein by reference.

Figure 3:
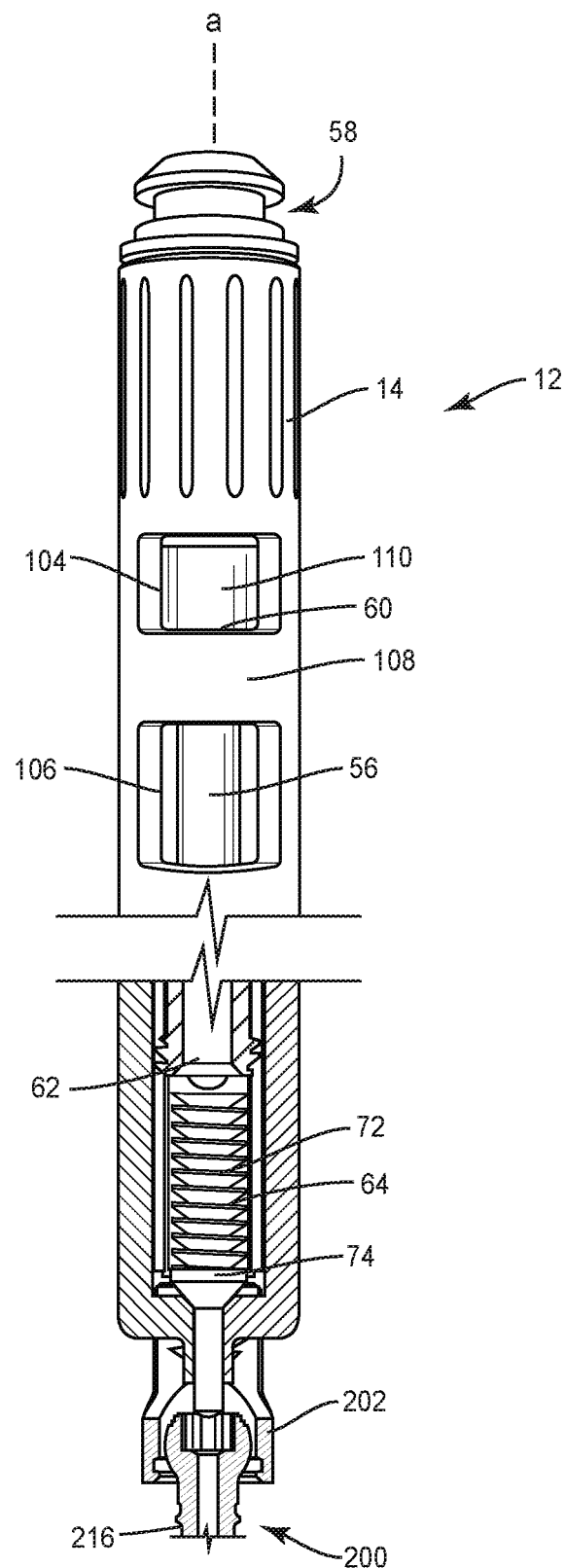
FIG. 3 is a side break away view of the components of one embodiment of a surgical system in accordance with the principles of the present disclosure.
Figure 9:
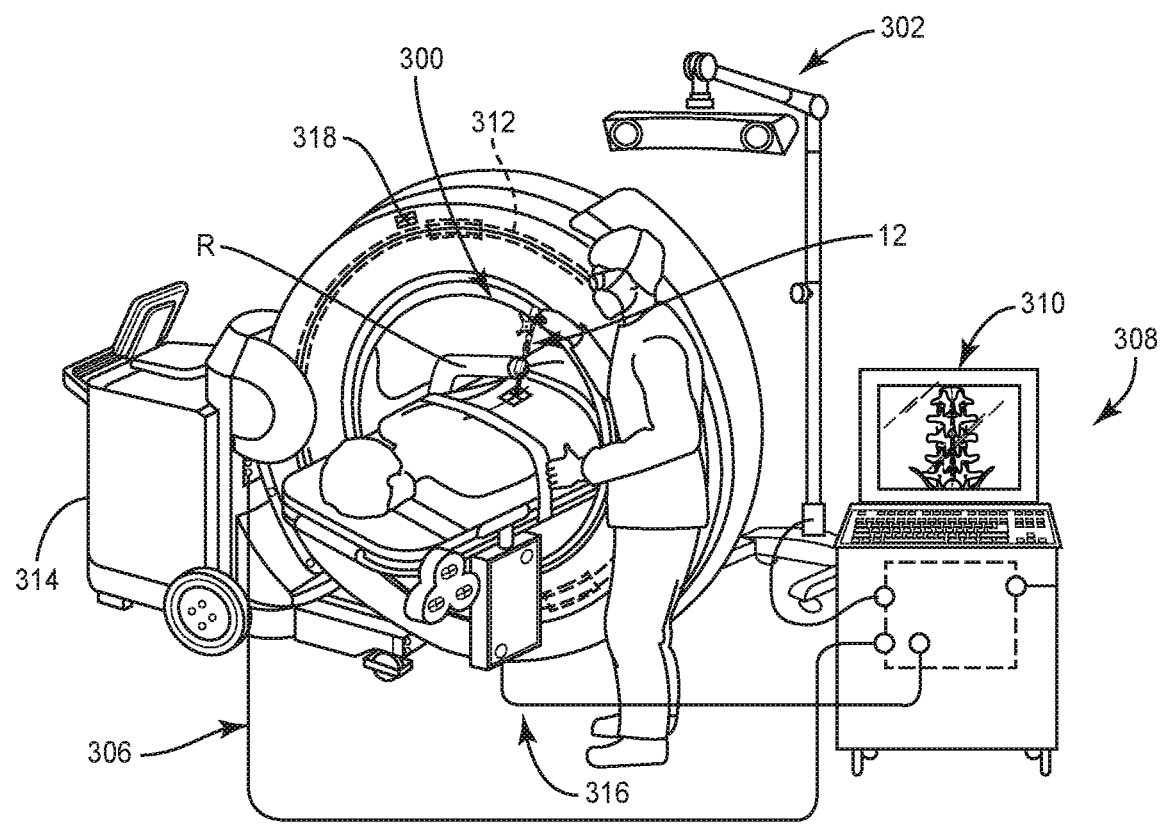
FIG. 9 is a perspective view of components of one embodiment of a surgical system in accordance with the principles of the present disclosure.

Outer sleeve 14 extends between a proximal end 18 and a distal end 20. Outer sleeve 14 defines a longitudinal axis a, as shown in FIG. 3. In some embodiments, outer sleeve 14 may have various configurations including, for example, round, oval, polygonal, irregular, consistent, variable, uniform and non-uniform. In some embodiments, outer sleeve 14 includes a diameter that is slightly larger than a screw spin diameter of bone fastener 200. This configuration allows bone fastener 200 and driver 12 to pass through an end effector of a robotic arm R, as shown in FIG. 9.

Figure 6:
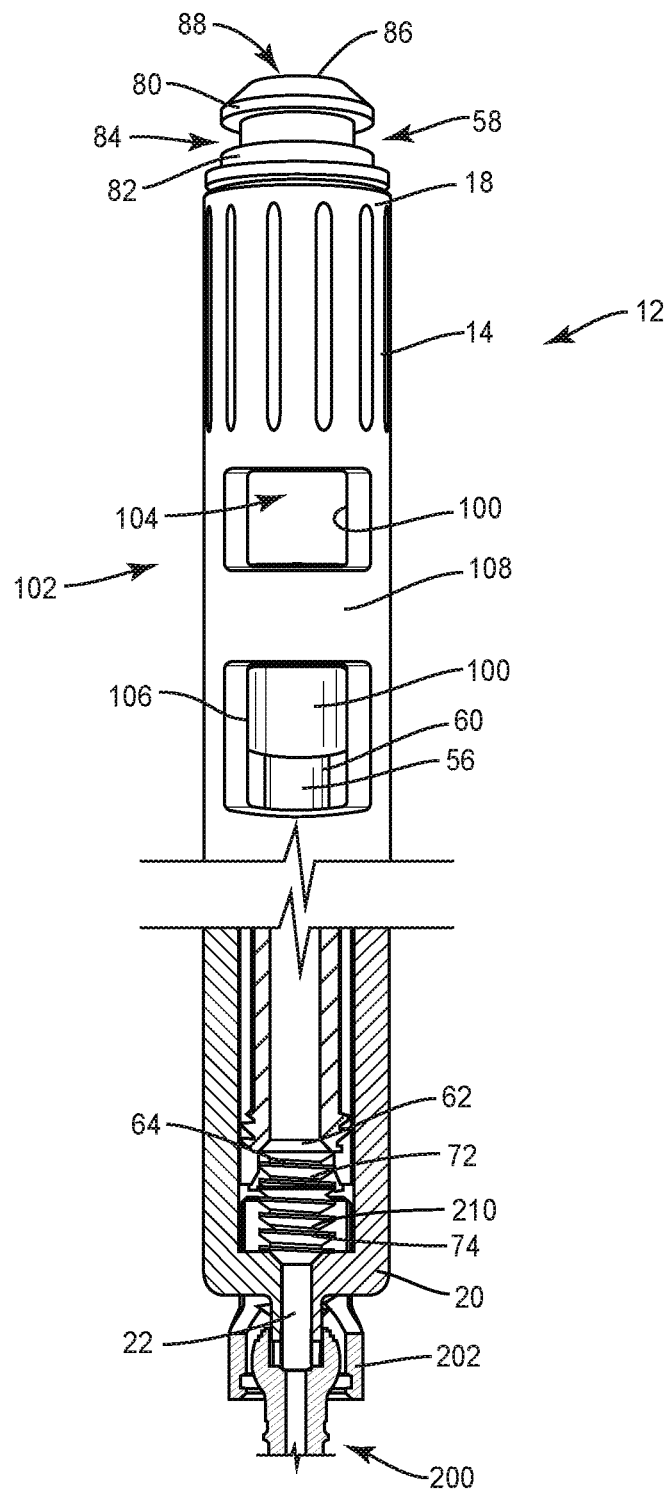
FIG. 6 is a side break away view of the components of one embodiment of a surgical system in accordance with the principles of the present disclosure.
Figure 8:
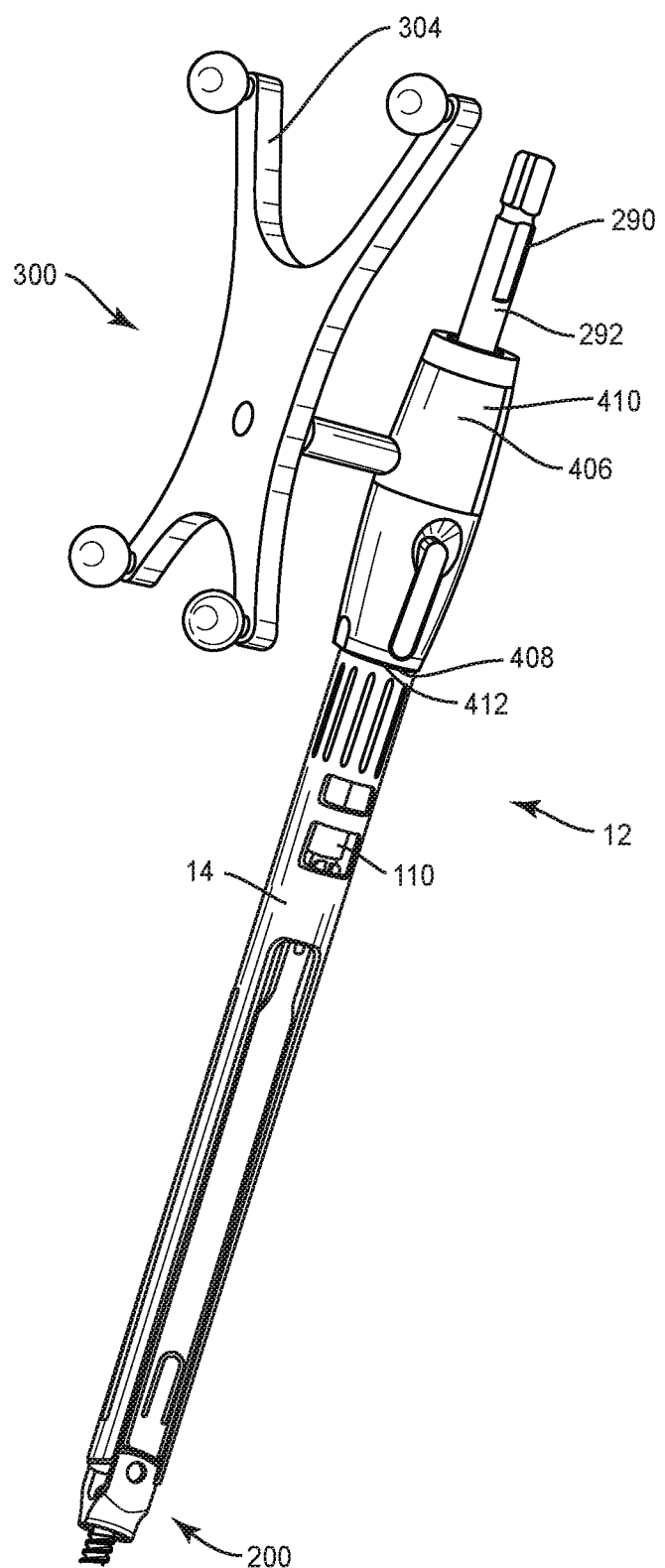
FIG. 8 is a perspective view of components of one embodiment of a surgical system in accordance with the principles of the present disclosure.

Outer sleeve 14 includes a surface 50 that defines a channel 52. Channel 52 is configured for disposal of inner shaft 56 and an engagement element, such as, for example, a screw 64, as described herein. Driver 12 includes a part 58 disposed with outer sleeve 14, as shown in FIG. 6. Part 58 is alternately connectable with an actuator and/or an adaptor attachable with an image guide, as described herein. Part 58 has a flange 80 and a flange 82 that is spaced apart from flange 80 by a recess 84. Part 58 has a surface 86 that defines a cavity 88 alternately configured for disposal of an actuator, such as, for example, a removable handle 90 therein and an adaptor, such as, for example, an adaptor 290 therein, as shown in FIG. 8. See also, the examples and disclosure of surgical instrument adaptors, spinal implant systems and methods shown and described in commonly owned and assigned U.S. patent application Ser. No. 16/163,645, filed Oct. 18, 2018, and published as U.S. Patent Application Publication 20200121396, on Apr. 23, 2020, the entire contents of which being incorporated herein by reference. Cavity 88 is in alignment with channel 52 to facilitate insertion of inner shaft 56 into end 18, through part 58 and into channel 52 for assembly, as described herein. Handle 90 is configured to actuate rotation of inner shaft 56 and screw 64, as described herein. Handle 90 includes a shaft 92 and a gripping portion 94 that is connected with shaft 92. Shaft 92 extends through part 58 such that shaft 92 is rotatable relative to part 58.

The indicia of driver 12 includes a marker, for example, a window 102 disposed with outer sleeve 14. Window 102 is configured for viewing a marker 110 disposed with inner shaft 56, as described herein. In some embodiments, window 102 includes a lateral opening 104 and a lateral opening 106. Openings 104, 106 are disposed axially along outer sleeve 14. Translation of inner shaft 56 relative to outer sleeve 14 aligns marker 110 relative to openings 104, 106, as described herein. Openings 104, 106 are separated by a flange 108. Alignment of marker 110 with opening 104 displays and/or indicates that driver 12 is in a release configuration relative to bone fastener 200, as described herein. Alignment of marker 110 with flange 108 displays and/or indicates driver 12 is in an intermediate configuration relative to bone fastener 200, as described herein. Alignment of marker 110 with opening 106 displays and/or indicates driver 12 is in a locked configuration relative to bone fastener 200, as described herein.

Figure 7:
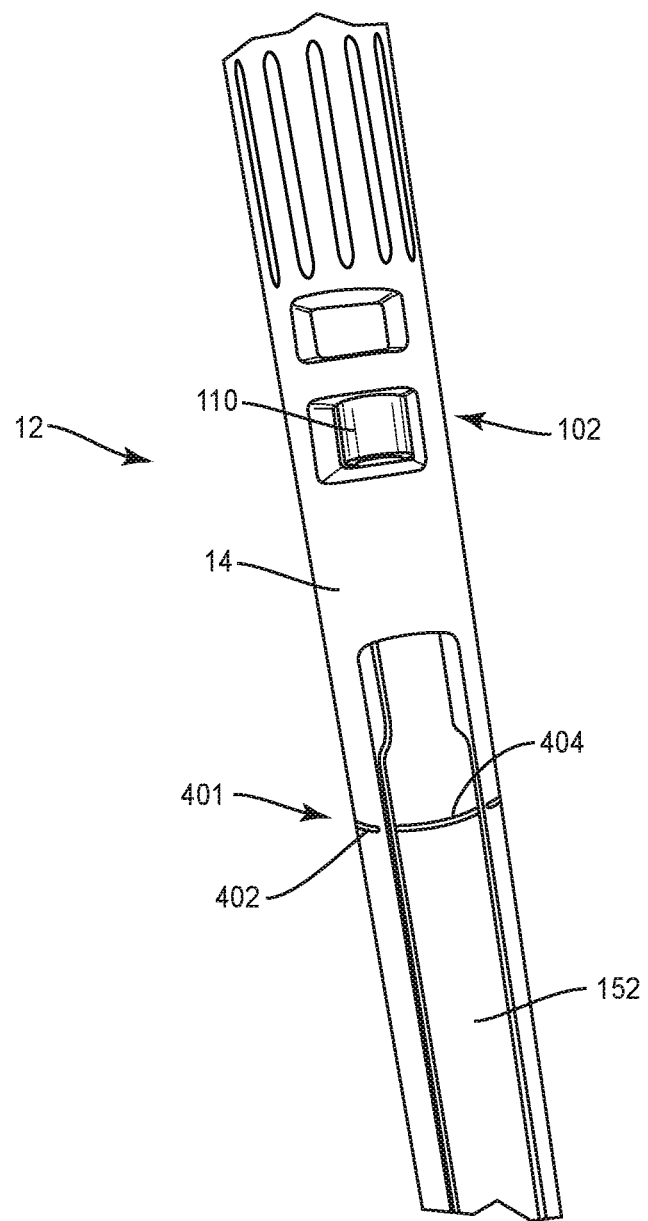
FIG. 7 is a side view of components of one embodiment of a surgical system in accordance with the principles of the present disclosure.

In some embodiments, outer sleeve 14 includes a marker 401, as shown in FIG. 7. In some embodiments, marker 401 includes a scoring 402 that is configured for alignment with marker including a scoring 404 disposed with extender tab 252 of a bone fastener assembly 250, as described herein. Alignment of scoring 402, 404 is configured to display and/or indicate proper alignment and connection of driver 12 with bone fastener assembly 250 such that screw 64 is selectively aligned with bone fastener 200.

In some embodiments, openings 104, 106 may be disposed at alternate orientations relative to axis a, such as, for example, transverse, perpendicular and/or other angular orientations such as acute or obtuse, and/or may be offset or staggered. In some embodiments, openings 104, 106 include a square configuration. In some embodiments, the markers described herein may have various configurations including, for example, round, oval, polygonal, irregular, consistent, variable, uniform and non-uniform. In some embodiments, the markers described herein may be transparent or semi-transparent. In some embodiments, the markers described herein may include visual indicia, scoring, readable visual indicia, tactile indicia.

End 20 of outer sleeve 14 includes a distal tip, such as, for example, drive 22. In some embodiments, drive 22 is integrally connected or monolithically formed with outer sleeve 14. This configuration facilitates control of tolerances to optimize accuracy of the connection of outer sleeve 14 with bone fastener 200. In some embodiments, drive 22 is removably connected with outer sleeve 14. Drive 22 is engageable with a spinal implant, such as, for example, bone fastener 200. For example, drive 22 fits with and is engageable with a mating surface, such as, for example, a socket 210 of bone fastener 200. Rotation of outer sleeve 14 simultaneously rotates drive 22 to drive, torque, insert or otherwise connect bone fastener 200 with tissue, as described herein. In some embodiments, drive 22 includes a hexalobe geometry for a mating engagement with a correspondingly shaped socket 210. In some embodiments, drive 22 can alternatively include a cruciform, phillips, square, hexagonal, polygonal, star cross sectional configuration for disposal of a correspondingly shaped socket 210.

Outer sleeve 14 includes an extension 30 and an extension 32. Extensions 30, 32 include a wall 34 having a surface 36. Surface 36 is connectable with an implant support, such as, for example, an extender tab 152 and an extender tab 152a, as described herein. Surface 36 defines a mating groove, such as, for example, pockets 38 configured for engagement with extender tabs 152, 152a, as described herein. Surface 36 is configured to resist and/or prevent disengagement of extender tabs 152, 152a from pocket 38, as described herein.

Pockets 38 are configured for engagement with extender tabs 152, 152a. Disposal of extender tabs 152, 152a with pockets 38 is configured to resist and/or prevent extender tabs 152, 152a from increasing the diameter of driver 12 when engaged with driver 12. In some embodiments, pockets 38 are disposed parallel to axis a. In some embodiments, pockets 38 are disposed at alternate orientations relative to axis a, such as, for example, at transverse, perpendicular and/or other angular orientations such as acute or obtuse, and/or may be offset or staggered.

Inner shaft 56 extends between an end 60 and an end 62. End 60 is engageable with shaft 92 for rotation of inner shaft 56 and screw 64, as described herein. Shaft 92 includes a surface 96 that engages a surface 66 of inner shaft 56 in an interference fit to facilitate simultaneous rotation of handle 90 and inner shaft 56. In some embodiments, shaft 92 includes various configurations, such as, for example, hexalobe, cruciform, phillips, square, hexagonal, polygonal, star cross sectional configuration for a mating engagement with correspondingly shaped portion of surface 66. In some embodiments, a distal end of handle 90 includes a punch 98 that is connected with shaft 92. Punch 98 has a maximum diameter that is less than a maximum diameter of shaft 92. Punch 98 is configured to dislodge material, such as, for example, cement that may trapped in a tip of driver 12.

End 60 includes marker 110 configured for alignment with window 102 to indicate and/or display the orientation of inner shaft 56 relative to outer sleeve 14 and bone fastener 200. In some embodiments, marker 110 includes visual indicia, such as, for example, a proximal end cap, a colored portion, scoring, readable visual indicia, tactile indicia or audible indicia. Marker 110 is aligned and viewable through openings 104, 106. Inner shaft 56 and screw 64 are configured for movement relative to outer sleeve 14. Inner shaft 56 translates screw 64 relative to outer sleeve 14 and bone fastener 200. Marker 110 translates into alignment with openings 104, 106 and flange 108 to indicate an orientation of screw 64 relative to a receiver 202 of bone fastener 200, as described herein.

Screw 64 includes an outer surface having an engagement element, such as, for example, a thread form 72. Thread form 72 is configured for engagement with a mating surface, such as, for example, thread forms of arms 204, 206 of bone fastener 200 to pull and or draw bone fastener 200 into engagement with driver 12, as described herein. Thread form 72 includes a leading portion 74.

Bone fastener 200 includes a receiver 202. Receiver 202 extends along axis a when connected with outer sleeve 14. Receiver 102 includes arms 204, 206. Arms 204, 206 define an implant cavity configured for disposal of a component of a spinal construct, such as, for example, a spinal rod (not shown). Receiver 202 includes an inner surface having a thread form located adjacent arm 204 and a thread form located adjacent arm 206. The thread forms of arms 204, 206 are configured for engagement with thread form 72 to retain bone fastener 200 with driver 12, as described herein. Bone fastener 200 includes threaded shaft 216. Shaft 216 is configured to penetrate tissue, such as, for example, bone.

In some embodiments, arms 204, 206 each include a break away tab (not shown) that is frangibly connected to arms 204, 206 such that manipulation of the break away tabs relative to arms 204, 206 can fracture and separate the break away tabs from arms 204, 206 at a predetermined force and/or torque limit, as described herein. In some embodiments, as force and/or torque is applied to the break away tabs and resistance increases, for example, the predetermined torque and force limit is approached.

In some embodiments, the break away tabs can fracture and separate at a predetermined force or torque limit, which may be in a range of approximately 2 Newton meters (N-m) to 8 N-m. In some embodiments, the break away tabs and arms 204, 206 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of the break away tabs.

A bone fastener assembly 250 includes extender tabs 252 connected with bone fastener 200. Extender tabs 252 extend between a proximal end 272 and a distal end 274. Proximal end 272 includes spring tips (not shown). The spring tips are aligned and disposable with pockets 38. Surface 36 is configured to resist and/or prevent disengagement of the spring tips, as described herein. Distal ends 274 are configured for slidable disposal of a portion of bone fastener 200, such as, for example, the break away tabs. In some embodiments, the break away tabs are configured to releasably fix extender tabs 252 with bone fastener 200 for connection with outer sleeve 14.

For example, in use, bone fastener assembly 250 can be connected with driver 12, as described herein, and drive 22 is oriented for engagement with socket 210. Drive 22 is engaged with socket 210 and screw 64 is disposed with inner shaft 56 and assembled with outer sleeve 14 for axial translation relative to outer sleeve 14 and along inner shaft 56 between a release configuration, which can include an eject position, as shown in FIG. 3, and a locked configuration, which can include a fully threaded position, as shown in FIG. 6, with bone fastener 200. Marker 110 is aligned with opening 102 in the release configuration displaying and/or indicating that screw 64 is translatable within channel 52 and relative to outer sleeve 14. In some embodiments, this configuration allows drive 22 to engage socket 210 prior to fixation of screw 64 with bone fastener 200.

With bone fastener assembly 250 connected with outer sleeve 14, thread form 72 is aligned with the thread forms of arms 204, 206 for engagement therebetween to retain bone fastener 200 with driver 12. Screw 64 is rotated simultaneously with inner shaft 56 by handle 90. Handle 90 is manipulated for rotation such that inner shaft 56 rotates screw 64 relative to and independent of outer sleeve 14. Thread form 72 engages the thread forms of arms 204, 206 and screw 64 axially translates into receiver 202 and relative to inner shaft 56. The threaded engagement of screw 64 and receiver 202 pulls and/or draws bone fastener 200 into the locked configuration with driver 12 for releasable fixation therebetween. Marker 110 is aligned with opening 104 in the locked configuration displaying and/or indicating that screw 64 is oriented in a fully threaded position with receiver 202, which includes a rigid connection.

Drive 22 is rotated to drive, torque, insert or otherwise connect bone fastener 200 with adjacent vertebral tissue. Screw 64 remains releasably fixed with receiver 202, independent of outer sleeve 14 rotation and/or engagement or friction with components of spinal implant system 10 as described herein, to resist and/or prevent disengagement or unthreading of screw 64 from receiver 202.

Figure 5:
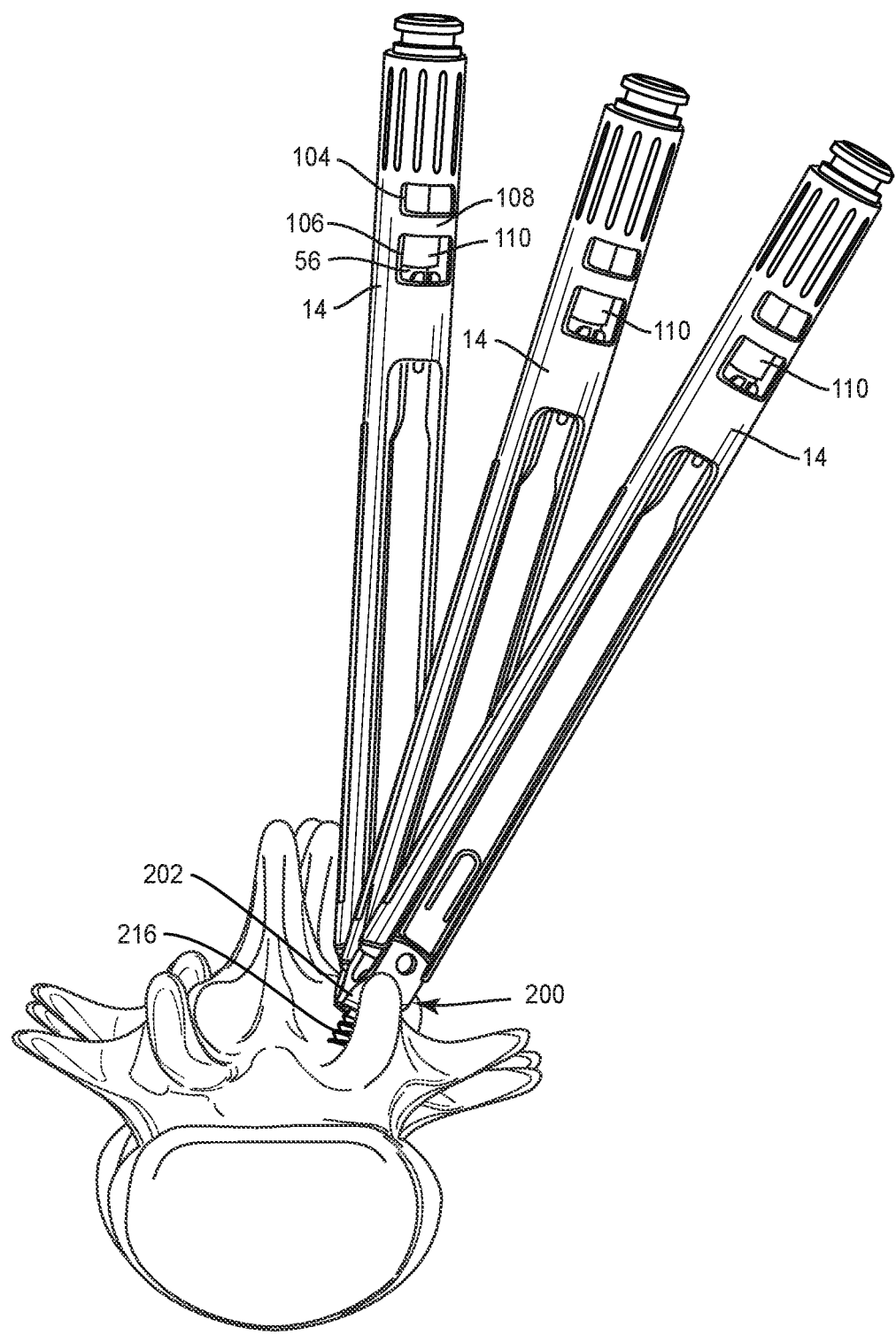
FIG. 5 is a perspective view of components of one embodiment of a surgical system in accordance with the principles of the present disclosure.

In some cases, a plurality of drivers 12 can be rigidly connected with bone fasteners 200 in the locked configuration, and attempted manipulation of the drivers 12 may be prevented due to the close proximity of the drivers 12 with vertebral tissue. For example, during a surgical procedure, manipulation of one or more drivers 12 may encounter resistance and/or be prevented, for example, due to a vertebral curve that causes engagement and/or interference between adjacent drivers 12 connected with a spine, as shown in FIG. 5.

Figure 4:
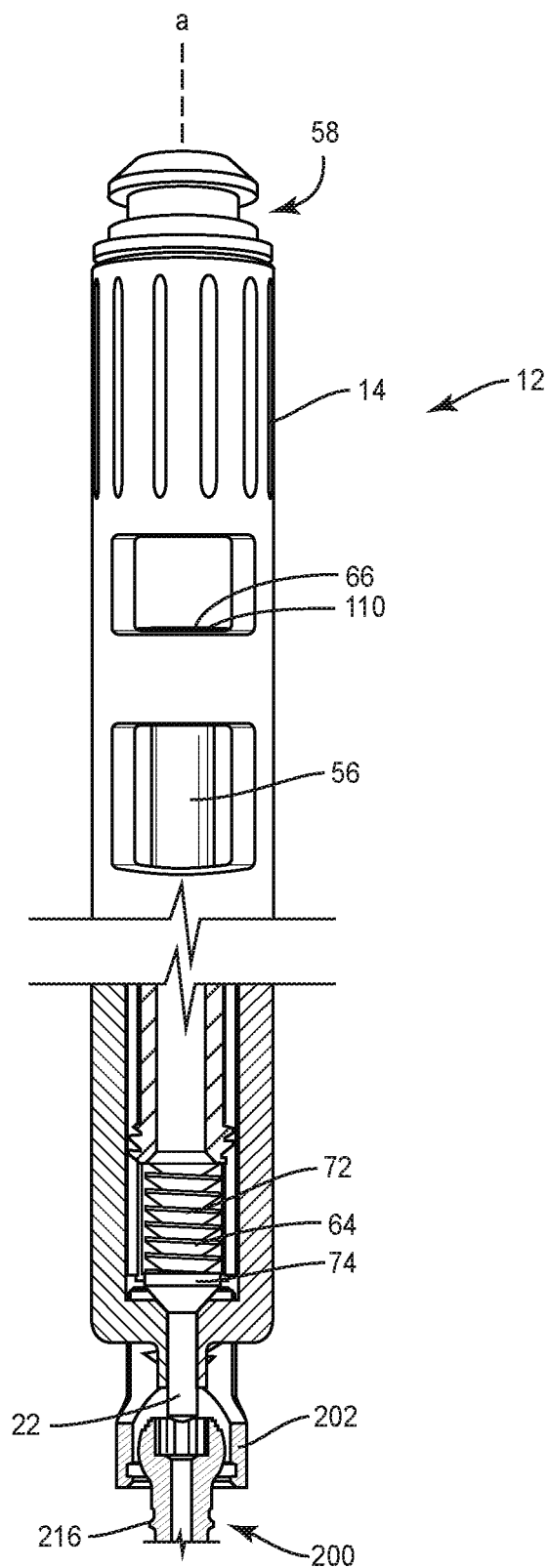
FIG. 4 is a side break away view of the components of one embodiment of a surgical system in accordance with the principles of the present disclosure.

In some embodiments, to overcome such engagement and/or interference between adjacent drivers 12, one or more drivers 12 can be disposed with bone fastener 200 in an intermediate configuration, which includes a partially threaded position, as shown in FIG. 4. Handle 90 is manipulated to partially disengage thread form 72 from receiver 202. Leading portion 74 remains engaged with receiver 202. Marker 110 is aligned with flange 108 in the intermediate configuration displaying and/or indicating that screw 64 is partially threaded with receiver 202. Positioning of screw 64 in the intermediate configuration allows for movement of one or more drivers 12 and respective receivers 202 in a flexible or loosened state of driver 12 with bone fastener 200. The intermediate configuration allows driver 12 to utilize a multi-axial range of motion of bone fastener 200 to counter the engagement and/or interference between adjacent drivers 12 such that one or more drivers 12 can be selectively manipulated. In some embodiments, from the intermediate configuration, driver 12 can be tightened with bone fastener 200 to the locking configuration, or loosened with bone fastener 200 to the non-locking configuration, for ejecting driver 12 from bone fastener 200.

In some embodiments, as shown in FIG. 8, handle 90 is removed from inner shaft 56, sleeve 14 and part 58 after screw 64 is moved from the release configuration to the locked configuration and an instrument, such as, for example, adaptor 290 is connected with driver 12 by inserting adaptor 290 through part 58. Adaptor 290 is configured to connect an image guide, for example, a navigation component 300 to driver 12 and/or to connect an actuator to driver 12. Adaptor 290 is fixed relative to shaft 56 and is rotatable relative to part 58. In some embodiments, adaptor 290 is connected to shaft 56 such that adaptor 290 is fixed relative to shaft 56 such that rotation of adaptor 290 also rotates shaft 56.

In some embodiments, driver 12 includes navigation component 300, as shown in FIGS. 8 and 9. Navigation component 300 is configured to connect to adaptor 290 and part 58 to couple navigation component 300 to driver 12, as discussed herein. Driver 12 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 200 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 300 is connected with adaptor 290 or part 58 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of a surgical navigation system 306, as shown in FIG. 9 and described herein. In some embodiments, the signal generated by emitter array 304 represents a position of bone fastener 200 relative to driver 12 and relative to tissue, such as, for example, bone. In some embodiments, the signal generated by emitter array 304 represents a three dimensional position of bone fastener 200 relative to tissue.

In some embodiments, sensor array 302 receives signals from emitter array 304 to provide a three-dimensional spatial position and/or a trajectory of bone fastener 200 relative to driver 12 and/or tissue. Emitter array 304 communicates with a processor of computer 308 of navigation system 306 to generate data for display of an image on monitor 310, as described herein. In some embodiments, sensor array 302 receives signals from emitter array 304 to provide a visual representation of a position of bone fastener 200 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, such as, for example, x-ray images appropriate for a given surgical procedure. In some embodiments, pre-acquired images of a patient are collected. In some embodiments, surgical navigation system 306 can include an O-ARM® imaging device 320 sold by Medtronic Navigation, Inc. having a place of business in Louisville, Colo., USA. Imaging device 320 may have a generally annular gantry housing that encloses an image capturing portion 312.

In some embodiments, navigation system 306 comprises an image capturing portion 314 that may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893; 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 318, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 314 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 200 relative to driver 12 and/or tissue can be tracked. Sensor array 302 is located in such a manner to provide a clear line of sight with emitter array 304, as described herein. In some embodiments, fiducial markers 330 of emitter array 304 communicate with sensor array 302 via infrared technology. Sensor array 302 is coupled to computer 308, which may be programmed with software modules that analyze signals transmitted by sensor array 302 to determine the position of each object in a detector space.

Navigation component 300 includes a collar 406 having an inner surface 408 and an outer surface 410. Surface 408 defines a passageway 412. Surface 408 is configured for releasable engagement with part 58, as discussed herein. Passageway 412 is configured to receive part 58. Surface 408 defines a lock, such as, for example, at least one resilient prong or tab (not shown). Navigation component 300 is connected with adaptor 290 and driver 12, as discussed herein.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving bone fasteners 200. One or more bone fastener assemblies 250 may connected with one or more respective drivers 12, as described herein. Drive 22 is engaged with socket 210 and screw 64 is disposed in a non-locking configuration or release configuration, as described herein, such that screw 64 is translatable relative to inner shaft 56 within channel 52 and rotatable relative to outer sleeve 14. Alignment of marker 110 with opening 104 provides visual confirmation of the release configuration.

With bone fastener assembly 250 connected with outer sleeve 14, handle 90 is manipulated for rotation such that inner shaft 56 rotates screw 64 relative to and independent of outer sleeve 14, as described herein. Threaded engagement of screw 64 and receiver 202 pulls and/or draws bone fastener 200 into the locked configuration, as described herein, with driver 12 for releasable fixation therebetween. Alignment of marker 110 with opening 106 provides visual confirmation of the locked configuration.

During the surgical procedure, one or more drivers 12 may be manipulated in connection with a surgical treatment of vertebrae. Such manipulation of the drivers 12 may encounter resistance and/or be prevented due to a vertebral curve of the vertebrae that causes engagement and/or interference between adjacent drivers 12 connected with a spine, as shown in FIG. 5. To overcome such engagement and/or interference between adjacent drivers 12, one or more drivers 12 can be disposed with bone fastener 200 in the intermediate configuration, as described herein. As such, handle 90 is manipulated to disengage thread form 72 from receiver 202. Leading portion 74 remains engaged with receiver 202 in the partially engaged configuration. Alignment of marker 110 with collar 108 provides visual confirmation of the intermediate configuration.

Handle 90 is removed from driver 12 and adaptor 290 is connected with driver 12, as described herein. Navigation component 300 is connected with driver 12, as described herein. Driver 12, connected with bone fastener assembly 250, is oriented for disposal with the end effector of robotic arm R, as described herein. The assembly of driver 12/bone fastener assembly 250 are disposed with robotic arm R for implantation of bone fasteners 200 with vertebrae employing robotic arm R and/or surgical navigation system 306, as described herein. An actuator is connected with shaft 292 of adaptor 290 and drive 22 engages bone fastener 200, as described herein, and outer sleeve 14 is rotated to drive, torque, insert or otherwise connect bone fastener 200 with adjacent tissue. Screw 64 remains releasably fixed with receiver 202, independent of outer sleeve 14 rotation and/or engagement or friction with the end effector to resist and/or prevent disengagement or unthreading of screw 64 from receiver 202.

In some embodiments, driver 12 is manipulated to deliver one or more bone fasteners 200 to a surgical site including vertebrae. Sensor array 302 receives signals from navigation component 300 to provide a three-dimensional spatial position and/or a trajectory of the assembly of driver 12/bone fastener assembly 250, which may be disposed with the end effector, relative to vertebrae and/or components of spinal implant system 10 for display on monitor 310.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:
   a surgical instrument comprising a first member, the first member defining a channel, the first member including a proximal end and an opposite distal end engageable with a first mating surface of a bone fastener, the surgical instrument comprising a second member disposed in the channel, the second member including an element engageable with a second mating surface of the bone fastener; and
   a navigation component coupled to the surgical instrument such that the second member extends through the navigation component, the navigation component being configured to generate a signal representative of a position of the bone fastener relative to the surgical instrument,
   wherein the first mating surface defines a socket configured for disposal of a tip of the distal end, the element defining a thread form configured to mate with spaced apart thread forms of the bone fastener, the second mating surface defining the thread forms of the bone fastener.

2. The surgical system recited in claim 1, wherein the second member is rotatable relative to the first member.

3. The surgical system recited in claim 1, wherein the proximal end comprises an engagement portion, the engagement portion comprising first and second flanges, the flanges being spaced apart by a recess, the navigation component being releasably coupled to the engagement portion.

4. The surgical system recited in claim 1, wherein the proximal end comprises a body and a part removably coupled to the body, the navigation component being releasably coupled to the part.

5. The surgical system recited in claim 1, wherein the second member comprises a proximal section and a distal section, the distal section including the element, the proximal section extending through the navigation component.

6. The surgical system recited in claim 5, wherein the proximal section is fixed to the distal section such that rotation of the proximal section relative to the first member rotates the distal section relative to the first member.

7. The surgical system recited in claim 5, wherein the proximal section comprises a drive bit engageable with a driver to rotate the second member relative to the first member.

8. The surgical system recited in claim 1, wherein rotation of the first member relative to the second member rotates the first mating surface relative to the second member, the socket being defined by the first mating surface.

9. The surgical system recited in claim 1, wherein the surgical instrument further comprises indicia of an orientation of the first and second members with the bone fastener.

10. The surgical system recited in claim 9, wherein the indicia includes a marker of the first member and a marker of the second member.

11. The surgical system recited in claim 1, wherein the surgical instrument further comprises indicia of alignment and tightening of the element and the second mating surface.

12. The surgical system recited in claim 11, wherein the indicia includes axially alignable scoring of the first and second members.

13. A surgical system comprising:
    a bone fastener comprising a first mating surface and a second mating surface;
    a surgical instrument comprising a first member, the first member defining a channel, the first member including a proximal end and an opposite distal end engageable with the first mating surface, the surgical instrument comprising a second member disposed in the channel, the second member including an element engageable with the second mating surface; and a navigation component coupled to the surgical instrument such that the second member extends through the navigation component, the navigation component being configured to generate a signal representative of a position of the bone fastener relative to the surgical instrument, wherein the first member comprises an extension, the extension including a wall having a surface that defines a pocket configured for engagement with an extension tab of the bone fastener.

14. The surgical system recited in claim 13, wherein the extension tab comprises spring tips, the spring tips being configured for disposal in the pocket.

15. The surgical system recited in claim 13, wherein the distal end comprises a tip configured for disposal in a socket of the bone fastener such that rotation of the first member relative to the second member rotates the first mating surface relative to the second member, the socket being defined by the first mating surface.

16. The surgical system recited in claim 13, wherein the first mating surface defines a socket configured for disposal of a tip of the distal end, the element defining a thread form configured to mate with spaced apart thread forms of the bone fastener, the second mating surface defining the thread forms of the bone fastener.

17. The surgical system recited in claim 16, wherein the bone fastener comprises spaced apart arms, the arms each including one of the thread forms of the bone fastener.

18. The surgical system recited in claim 13, wherein the bone fastener comprises a screw and a receiver, the screw being positioned within the receiver such that the screw is rotatable relative to the receiver, the screw including the first mating surface, the receiving including the second mating surface.

19. A surgical system comprising:

a surgical instrument comprising a first member, the first member defining a channel, the first member including a proximal end and an opposite distal end engageable with a first mating surface of a bone fastener, the surgical instrument comprising a second member disposed in the channel, the second member including an element engageable with a second mating surface of the bone fastener; and a navigation component coupled to the surgical instrument such that the second member extends through the navigation component, the navigation component being configured to generate a signal representative of a position of the bone fastener relative to the surgical instrument, wherein the second member comprises a proximal section and a distal section, the distal section including the element, the proximal section extending through the navigation component, and wherein the element is a thread form and the proximal section comprises a drive bit engageable with a driver to rotate the second member relative to the first member.

20. The surgical system recited in claim 19, wherein the second member is rotatable relative to the first member.

21. The surgical system recited in claim 19, wherein the proximal end comprises an engagement portion, the engagement portion comprising first and second flanges, the flanges being spaced apart by a recess, the navigation component being releasably coupled to the engagement portion.

\* \* \* \* \*